United States Patent [19]
Heck

[11] 4,428,743
[45] Jan. 31, 1984

[54] FLOW-THROUGH CHAMBER

[75] Inventor: Wolfgang Heck, Hechingen, Fed. Rep. of Germany

[73] Assignee: Gambro Dialysatoren KG, Fed. Rep. of Germany

[21] Appl. No.: 343,897

[22] Filed: Jan. 29, 1982

[30] Foreign Application Priority Data

Feb. 16, 1981 [SE] Sweden .................................. 8101025

[51] Int. Cl.³ .............................................. A61M 5/00
[52] U.S. Cl. ......................................... 604/4; 604/122; 604/251; 141/286
[58] Field of Search ......... 128/DIG. 3; 604/4, 80–86, 604/246, 122, 251–254, 257; 222/158, 159; 141/374, 286

[56] References Cited

U.S. PATENT DOCUMENTS

| 1,171,047 | 7/1959 | Carrieri . | |
|---|---|---|---|
| 3,311,268 | 3/1967 | Fields | 604/122 X |
| 3,881,640 | 5/1975 | Noble | 222/158 |
| 3,896,733 | 7/1975 | Rosenberg | 604/4 |
| 3,965,895 | 6/1976 | Dabney | 141/374 X |
| 4,191,183 | 3/1980 | Mendelson | 604/83 X |

FOREIGN PATENT DOCUMENTS 438611  11/1930  United Kingdom ................ 604/251

Primary Examiner—Dalton L. Truluck
Attorney, Agent, or Firm—Lerner, David, Littenberg, Krumholz & Mentlik

[57] ABSTRACT

Flow-through chambers, such as drip or expansion chambers, which are intended to form part of a duct for blood or other such sensitive fluids, are disclosed. The chambers include a housing, an inlet, an outlet, and a flow directing portion of the housing for directing the flow of the fluid from the inlet to the outlet. The flow directing portion of the housing is formed in a manner so as to deflect the flow of the fluid from the inlet towards the outlet in a gradual manner so as to protect the fluid within the chamber.

6 Claims, 4 Drawing Figures

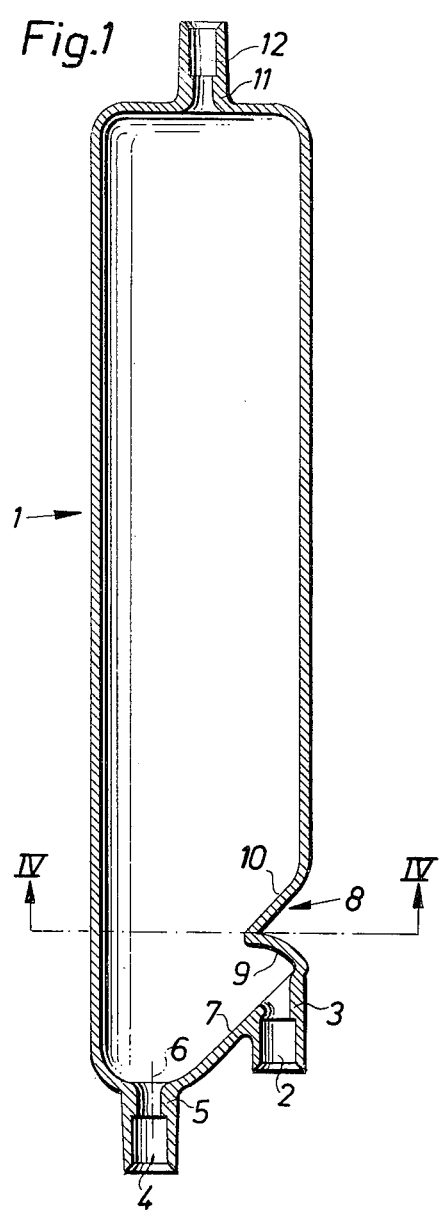
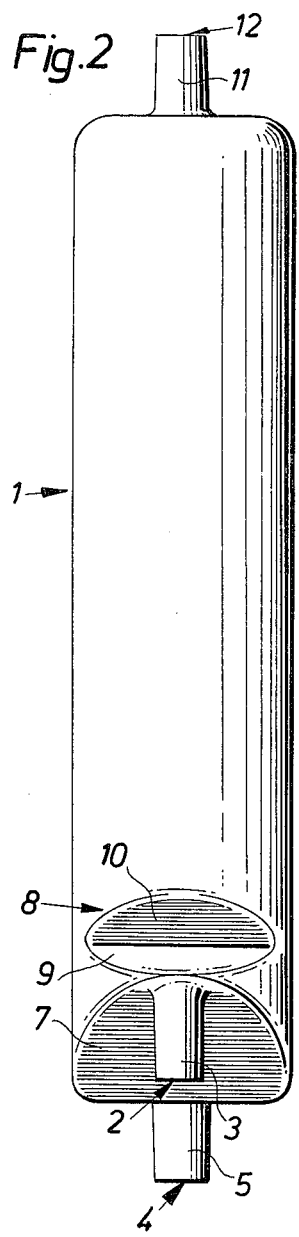
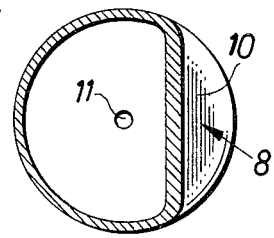
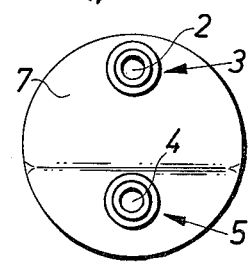

FLOW-THROUGH CHAMBER

FIELD OF THE INVENTION

The present invention relates to flow-through chambers, such as drip chambers or expansion chambers, which are intended to form part of a duct for blood or other such sensitive fluids. More particularly, the present invention relates to such flow-through chambers which include at least one inlet and at least one outlet and which further include means for directing fluid flow from the inlet to the outlet.

BACKGROUND OF THE INVENTION

In connection with dialysis and other such similar extracorporial blood treatment procedures, a patient is generally connected to the treatment machine or apparatus with the aid of a set of tubes which may include different types of chambers therein. These sets of tubes may, in addition to the above, also include different chambers for connection to different measuring instruments, such as pressure gauges or thermometers. While the discussion set forth below with respect to the present invention is thus specifically directed to a chamber of this type which is primarily intended for use as an expansion chamber, it will also be clear to those versed in this art that it can additionally be used for other purposes.

In connection with chambers of this type it is quite often considered to be very desirable to deflect the flow of fluid therein. In the past, this has normally been achieved with the aid of additional and/or separate parts which are fixed, in different ways, to the chamber itself.

BRIEF DESCRIPTION OF THE INVENTION

In accordance with the present invention, these objects have now been accomplished while at the same time loose or separate parts for deflecting the fluid flow within the chambers have now been eliminated. In particular, this has been accomplished by providing means for deflecting the fluid flow from the inlet to the outlet in the chamber which are formed by the wall of the chamber itself, and in particular, comprise a specially formed indentation forming part of the wall of the chamber itself.

Thus, in accordance with this invention, applicant has discovered a flow-through chamber for handling sensitive fluids such as blood which includes a housing including an inlet, an outlet and flow directing means for directing the flow of that fluid from the inlet to the outlet, the flow directing means comprising a portion of the housing itself formed in a manner so as to deflect the flow of fluid from the inlet towards the outlet in a gradual manner so as to protect the fluid within the chamber.

In accordance with one embodiment of the flow-through chamber of this invention the flow directing means comprises an indentation formed in the wall of the housing itself. Preferably, the housing including the flow directing means is formed by blow molding techniques.

In accordance with another embodiment of the flow-through chamber of the present invention the housing has an elongated shape having first and second ends. In a preferred embodiment, both the inlet and the outlet are located at the first end of the elongated housing so that the housing can be utilized in a vertical configuration with the first end located at the bottom thereof. In accordance with this embodiment, the inlet and outlet are preferably located parallel to each other at the first end of the elongated housing, and both include integral nozzle members. Preferably, the first end of the housing includes an oblique wall portion having first and second ends, the first end being lower than the second end when the housing is in its vertical configuration, with the outlet located at the first end of the oblique wall portion and the inlet being located at the second end of the oblique wall portion, whereby the outlet is located at the lowest point on the housing when it is in its vertical configuration.

In accordance with another embodiment of the flow-through chamber of the present invention, particularly when it is used as a drip chamber, the housing has an elongated shape having first and second ends, with the first end being located at the bottom of the chamber when it is in its vertical configuration, and with the inlet being located at the second end of the housing and the outlet being located at the first end of the housing, thereby defining a vertical path between the inlet and the outlet, and wherein the flow directing means projects into that vertical path so that the distance the fluid must drop from the inlet to the outlet is reduced when the level of fluid in the housing is below that of the flow directing means.

The chamber of the present invention is preferably manufactured by blow molding with simultaneous formation of the indented part or flow directing means. This can be achieved in a simple manner in that the blow mold is provided with an inwardly projecting portion corresponding to that of the desired indentation. Alternately, the chamber can also be manufactured, for example, by injection or vacuum molding techniques. In that case, it can appropriately be made in the form of two halves which can then be joined together.

The flow-through chamber of the present invention is preferably designed so that it has an elongated shape which is intended to be placed vertically with the inlet and the outlet arranged parallel to each other at the bottom end of the chamber in the form of nozzles which are designed as integral parts of the chamber. These nozzles are thus intended to be connected to tubing included in the set of tubes being utilized. This design is useful if the chamber is to be used, for example, as an expansion chamber.

Such expansion chambers may be required, for example, when a less expandable-type of dialyzer, such as a fiber dialyzer, is used in the so-called "single needle" technique. In such processes blood is intermittently taken from the patient alternately with being intermittently being returned to the patient in the same manner. Expansion chambers are required in such processes in order that the pressure in the dialyzer does not become too high. In many other types of dialyzers no such expansion chamber is required, since the dialyzer itself may be capable of expanding so as to prevent an increase in pressure therein.

In connection with the use of such expansion chambers as indicated above, the chambers are preferably provided with an inlet and an outlet arranged parallel to each other at the bottom of the elongated chamber when it is in its vertical configuration. In such embodiments, it is appropriate for the outlet to be arranged at the lowest point of the chamber while the inlet is arranged on a wall obliquely sloping towards that point. In connection with this design the means for deflecting the fluid flow can provide a very gentle curvature of the fluid path from the inlet to the outlet so as to ensure careful treatment of the blood while at the same time preventing frothing thereof.

The flow-through chamber of this invention can be substantially the same shape when it is to be used as a drip chamber. In this case, however, the inlet may be arranged at the top end of the chamber with the outlet at the bottom end. The same deflection means for the fluid flow can again be arranged so as to reduce the height of the fluid drop, i.e. if the fluid level within the chamber is located below the deflection means therein. Again, careful treatment of the blood or corresponding other sensitive fluid to be conducted through the chamber can be achieved. The flow directing means or indented portion of the housing may be designed so that it causes the fluid flow to run directly along the chamber wall instead of freely dropping down to the outlet from the inlet. For example, it may be gently curved.

BRIEF DESCRIPTION OF THE DRAWINGS

In connection with the following detailed description of the invention, it will be described in greater detail with reference to the enclosed drawings, showing a preferred embodiment of the subject matter of the present invention. In these drawings:

FIG. 1 is a side, elevational, longitudinal, sectional view of an expansion chamber in accordance with the present invention;

FIG. 2 is a side, elevational view of the expansion chamber shown in FIG. 1;

FIG. 3 is an end, elevational view of the expansion chamber shown in FIG. 2; and FIG. 4 is an end, elevational, sectional view of the expansion chamber shown in FIG. 1 taken along line IV—IV of FIG. 1.

DETAILED DESCRIPTION

Referring to the drawings, in which like numerals refer to like portions thereof, FIG. 1 shows an expansion chamber designed in accordance with the present invention. However, as it will be clear to those of ordinary skill in this art, this chamber, with certain minor modifications, can easily be altered to become, for example, a drip chamber or some other type of chamber which is to be included in the set of tubes of the aforementioned type.

The expansion chamber itself generally is designated 1, and is provided with an inlet 2 arranged in an inlet nozzle 3 and that outlet 4 arranged in an outlet nozzle 5. As can be seen in the drawings, the outlet is arranged so that it issues from the lowest point 6 of the chamber 1. In the same manner, it can be seen that the inlet 2 is arranged to open out into a wall 7 which slopes obliquely towards this low point 6.

The flow directing means or indentation which characterizes the present invention thus constitutes the specifically designed member for deflecting the fluid flow and is designated generally by the numeral 8. This flow directing means includes a lower wall portion 9 and an upper wall portion 10. The lower wall portion 10 of the fluid deflecting means 8, as seen from the inside of the chamber, includes a concave design so that the fluid flow will be gently deflected in the desired direction towards the outlet 4. The upper wall portion 10 of the fluid deflecting means 8 may, in principle, be of any desired shape.

In the particular example shown in the drawings, the expansion chamber is designed with a third nozzle 11 with an outlet 12 which may be connected, for example, to a pressure gauge for measuring the pressure within the chamber 1.

Of course, the present invention is not exclusively limited to the embodiment of the present invention shown in the drawings, but can be varied within the scope of the claims set forth below. As mentioned above, it will be clear to those of ordinary skill in this art that the chamber 1 can be readily modified for different uses. If, for example, the chamber is to be used in an upside-down configuration with respect to the drawings, the indentation 8 will then be appropriately designed with a more gentle curvature so as to force the fluid flow to follow the wall portions 9 and 10.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What is claimed is:

1. A flow-through chamber for handling sensitive liquids such as blood, comprising a housing including an inlet, an oulet and flow directing means for directing the flow of said liquid from said inlet to said outlet, said flow directing means comprising an indentation of one-piece construction formed by a portion of the wall of said housing, said flow directing means being formed in a manner so as to be positioned in the flow of said liquid between said inlet and said outlet to deflect the flow of said liquid from said inlet towards said outlet in a gradual manner so as to protect said liquid within said chamber.

2. The flow-through chamber of claim 1 wherein said housing has an elongated shape having a first end and a second end, with both said inlet and said outlet being located at said first end thereof, whereby said housing may be utilized in a vertical configuration with said first end being located at the bottom thereof.

3. The flow-through chamber of claim 2 wherein said inlet and said outlet are located parallel to each other at said first end of said housing, and said inlet and said outlet each include integral nozzle members.

4. The flow-through chamber of claim 1 wherein said housing has an elongated shape having a first end and a second end, whereby said housing may be utilized in a vertical configuration with said first end being located at the bottom thereof, and wherein said inlet is located at said second end of said housing, said outlet is located at said first end of said housing, thereby defining a vertical path between said inlet and said outlet, and said flow directing means projects into said vertical path whereby the distance which said fluid must drop from said inlet to said outlet is reduced when the level of fluid in said housing is below said flow directing means.

5. A flow-through chamber for handling sensitive fluids, comprising a housing including an inlet, an outlet and a flow directing means for directing the flow of said fluid from said inlet to said outlet, said flow directing means comprising a portion of said housing formed in a manner so as to deflect the flow of said fluid from said inlet towards said outlet in a gradual manner so as to protect said fluid within said chamber, said housing having an elongated shape having a first end and a second end, both said inlet and said outlet being located at said first end thereof, whereby said housing may be utilized in a vertical configuration with said first end being located at the bottom thereof, said first end of said housing including an oblique wall portion having a first end and a second end, said first end of said oblique wall portion being lower than said second end of said oblique wall portion when said housing is placed in said vertical configuration, with said outlet being located at said first end of said oblique wall portion and said inlet being located at said second end of said oblique wall portion, whereby said outlet is located at the lowest point of said housing.

6. The flow-through chamber of claim 1 wherein said inlet and said outlet are located parallel to each other at said first end of said housing, said inlet and said outlet each including integral nozzle members.

* * * * *

UNITED STATES PATENT AND TRADEMARK OFFICE
CERTIFICATE OF CORRECTION

PATENT NO. : 4,428,743

DATED : March 8, 1984

INVENTOR(S) : Wolfgang Heck

It is certified that error appears in the above-identified patent and that said Letters Patent is hereby corrected as shown below:

Column 6, line 5 "claim 1" should read -- claim 5 --.

Signed and Sealed this

Third Day of July 1984

[SEAL]

Attest:

GERALD J. MOSSINGHOFF

*Attesting Officer*  *Commissioner of Patents and Trademarks*